(12) United States Patent
Brandelik et al.

(10) Patent No.: US 6,507,200 B2
(45) Date of Patent: Jan. 14, 2003

(54) MOISTURE SENSOR FOR LAYERS

(75) Inventors: Alexander Brandelik, Karlsruhe (DE); Christof Hübner, Edingen-Neckarhausen (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/754,584

(22) Filed: Jan. 5, 2001

(65) Prior Publication Data
US 2001/0002105 A1 May 31, 2001

Related U.S. Application Data

(63) Continuation-in-part of application No. PCT/EP99/03704, filed on May 28, 1999.

(30) Foreign Application Priority Data
Jul. 24, 1998 (DE) .......................... 198 33 331

(51) Int. Cl.$^7$ .............................. C01R 27/08
(52) U.S. Cl. ............. 324/696; 324/634; 324/658
(58) Field of Search .................. 324/658, 661, 324/662, 664, 687, 694, 634, 696

(56) References Cited

U.S. PATENT DOCUMENTS

| | | | |
|---|---|---|---|
| 3,824,460 A | 7/1974 | Gustafson | 324/664 |
| 3,965,416 A | 6/1976 | Friedman | 324/633 |
| 4,749,731 A | * 6/1988 | Kyminas et al. | 524/31 |
| 5,073,756 A | 12/1991 | Brandelik | 324/643 |
| 5,459,403 A | * 10/1995 | Kohler et al. | 324/643 |
| 5,648,724 A | * 7/1997 | Yankielun et al. | 324/533 |

FOREIGN PATENT DOCUMENTS

| | | | |
|---|---|---|---|
| DE | 42 13 070 | 10/1993 | G01M/3/16 |
| EP | 0 342 013 | 11/1989 | C01M/3/40 |

OTHER PUBLICATIONS

"Advanced groung truth for snow and glacier sensing" Brandelik et al, Geoscience and Remote Sensing Symposium Proceesing, pp. 1873–1875 vol. 4, Jul. 6–10 1998.*

Kent, M. et al., "Broadband Measurement of Stripline Moisture Sensors", Journal of Microwave Power, Sep. 1984, Canada, Bd. 19, Nr. 4, pp. 173–179.

Brandeliak, A. et al., Sensing and Managing the Environment. 1998 IEEE International Geoscience and Remote Sensing. Symposium Proceedings. (Cat.No.98ch36174), Igrass '98. Sensing and Managine the Environment. 1998 IEEE International Geoscience and Remote Sensi, pp. 1873–1875, vol. 4, 1998, New York.

* cited by examiner

*Primary Examiner*—N. Le
*Assistant Examiner*—Walter Benson
(74) *Attorney, Agent, or Firm*—Klaus J. Bach

(57) ABSTRACT

In a moisture sensor for monitoring the moisture content of layers, at least two parallel electrical conductors connected to a measuring apparatus are disposed adjacent the layers to be monitored. The conductors are surrounded by an insulating material and carry, at their side remote from the layer whose dielectric coefficient is to be monitored, a metal shielding layer for limiting the measurement field of the sensor.

8 Claims, 1 Drawing Sheet

MOISTURE SENSOR FOR LAYERS

This is a continuation-in-part application of international application PCT/EP99/03704 filed May 28, 1999 and claiming the priority of German application 198 33 331.5 filed Jul. 24, 1998.

BACKGROUND OF THE INVENTION

The invention relates to a moisture sensor for layers, which moisture sensor comprises at least two parallel electrical conductors, a feeder cable and a measuring device for detecting dielectric coefficients.

For many applications, it is important to know the moisture content in thin material layers, which consist of a mixture of non-metallic solids material, water and air. A layer is considered to be thin if it can be rolled from a roll and layed out on an uneven surface, but is thicker than the largest fragmented solid material element which is disposed in the mixture with water and air.

Particularly important examples for these objects are geosynthetic clay or betonite mats. The collective denomination for these materials is geosynthetic (clay) liners. These mats, which typically have a thickness of about 4 mm to 30 mm, are preferably used as moisture and gas insulation in sealing arrangements of deposit bases and or/surfaces, for water retaining ponds, water ponds, dams, underwater installations and generally in civil engineering construction sites. These mats maintain their insulating capability as long as they do not dry out. In order to timely prevent their drying out, the moisture content of the mats alone must be continuously monitored without distortions by the construction materials above and below the mat. Generally, water is supplied to such a mat only at one side thereof. In this case, there may be a high gradient of the water content throughout the thickness of the mat without a loss of isolation quality. As a result, moisture content differences within the mat itself also need to be monitored.

The conference presentation "Measuring the In-situ Moisture Content of Geosynthetic Clay Liners (GCLS) Using Time Domain Reflectometry", Matthew A. Eberle and Kent P. von Maubeuge, in 1998 Sixth International Conference on Geosynthetics, Mar. 25–29, 1998, Atlanta, USA represents adequately today's state of the art: The signal travel time along an electric conductor is measured which is inserted into the material to be monitored. The time determined in this way depends on the dielectric coefficient DK of the material to be monitored and the dielectric coefficient depends on the moisture content of the material.

The problems and disadvantages of the experiments described therein are as follows:
a) The electric measuring field extends beyond the mat layer thickness so that the materials below and above the mat have a falsifying influence on measuring result.
b) It is difficult to insert the measuring electrode of the probe exactly into the center of the mat.
c) The insertion probe can monitor only over relatively short non-representative length because the probe is rigid so that it cannot follow the mat-shape which is generally uneven.
d) It is known that air bubbles and air gaps between the probe and the material, whose formation is unavoidable when the probe is inserted, falsify the measuring value to a substantial degree which, furthermore, changes over time.
e) The measuring curve of the measuring impulse shown in the publication indicates that the determination of the pulse travel time, which is indicative of the moisture content, is not certain, since the attenuation along the measuring electrode is too high and because there is too much of an uncontrollable mismatch of the impedances between the probe and the measuring apparatus.

These problems and disadvantages are the reason that standard measuring probes for that purpose are commercially not yet available.

A weather report should include reports regarding the freezing conditions of the ground and the ice formation on objects close to the ground. The weather service therefore needs automatic icing sensors, which can distinguish between the conditions dry, moist, and frozen. At the present time, the German weather service determines these conditions by subjective observation. This method, however, should be replaced by objective automatic measuring methods.

A feasibility study of intelligent sensors for measuring the ground condition by icing sensors, which was prepared by STS Systemtechnik Schwerin GmbH as ordered by the German weather service, Hamburg, 1997 describes a proposal wherein the propagation of sound (velocity and reflection) in a solid material, which is either dry or covered by a layer of water or ice, is measured. However, since the sound impedances of the three conditions have a relationship like 3.2 to 4 and to 1.5, a relatively complicated instrumentation is needed in order to employ these distinctions. The apparatus is therefore relatively expensive.

The company Vaisala TMI Ltd, 349 Bristol Rd, Birmingham B57SW, UK offers a measuring system for road condition reports under the name IceCast Ice Prediction System. This system includes a probe, which measures different parameters such as electric conductivity, polarization, DK, temperature of the street surface, depending on the condition. From these many data, a prediction of an ice formation danger is calculated. The system is complicated and very expensive. The apparatus is not suitable for measuring icing conditions near the ground.

The company Boschung Verkehrstechnik GmbH, L ützowgasse 14 A-1140 Wien, Austria distributes a measuring system also for the prediction of road conditions. However, this system is also very complicated. Among others, it uses a procedure, wherein an isolated ground element is subjected to heating and cooling by Peltier elements. Also this system is unsuitable for monitoring ice formation near the ground.

It is the object of the present invention to determine the actual condition of the ground surface and the icing of objects close to the ground and to provide a sensor by which the moisture can be determined from the outside.

SUMMARY OF THE INVENTION

In a moisture sensor for monitoring the moisture content of layers, at least two parallel electrical conductors connected to a measuring apparatus are disposed adjacent the layers to be monitored. The conductors are surrounded by an insulating material and carry a metal shielding layer at their side remote from the layer whose dielectric coefficient is to be monitored for limiting the measurement field of the sensor.

The probe according to the invention has the following advantages:
a) The electrodes (sensor, probe) are flexible. The probe can be disposed on an uneven surface of a material to be monitored like a flexible flat cable.
b) The electrodes of the probe are provided with an electric insulative coating and disposed at a constant distance from each other, whereby the electrical attenuation along the electrodes is kept relatively small. The small attenuation makes the construction of relatively long probes possible, which deliver representative monitoring results. The finite thickness of the insulation coating facilitates the provision of a metal shielding layer, whereby the electric field of the electrodes is shielded from the adjacent space without a direct short circuit and without a reduction of the measuring sensitivity. Then, the probe has a one-sided sensitivity. In this way, the probe does not need to be inserted into the material. Only a small engagement pressure is needed to avoid the formation of air gaps, which may falsify the measuring results.

c) By optimizing the distance between the electrodes and also the thickness of the insulation layer, the probe can be adjusted to the thickness of the material to be measured with good impedance adaptation between the probe and the measuring apparatus. If necessary, or if there are doubts concerning the penetration depth of the measuring field, the one-sided measuring field can be limited to the thickness of the material. In that case, the material is covered also on top with a metallic foil.

d) In order to reduce external electric disturbances, preferably a three conductor arrangement is utilized (See the report of Eberle and V. Meubeuge referred to above). If, in accordance with the invention, the center electrode of the three conductor arrangement is formed by the two adjacent conductors of two electrode pairs arranged in parallel, another parameter is available, that is the distance between the electrode pairs. With the selection of this distance, the impedance of the probe arrangement can be advantageously selected for good adaptation.

The moisture sensor for layers becomes an icing detector in that a porous, water storing material layer is employed in place of the material layer to be measured. The porous material layer should consist of a non-metallic material, which has a low dielectric co-efficient DK and a very small volume proportion in a layer of about 5–10 mm thickness. Filter mats of polyester fibers with an area weight of 300 g/m$^2$ and a thickness of 20 mm have been found to be suitable. The air-containing pores in this layer should be so small that, with the given surface tension of the water, raindrops can enter the pores but are retained within the layer. The DK of the layer in a dry state is only negligibly greater than 1, which is the DK of air. When exposed to rain, a water layer is formed within the porous material. The DK of the layer is then about 80, which is the DK of water. At temperatures below the freezing point, the water is converted to ice. As a result, the DK of the layer will be about 3.15, which is the DK of ice. The water evaporation from the porous mat in comparison with the evaporation from an exposed water surface is only negligibly delayed.

The solution described herein utilized the differences of the DK values for the above-referred to states, (dry, moist, ice), which differ from one another like the number 1 to 80 and to 3.15. This increased dynamic permits a simplified instrumentation when compared with the solutions described above. If two moisture sensors are used as icing detectors, one would be placed on the ground while the other would be suspended in the air close to the ground. In this way, a distinction can be made between icing on the ground and icing in the air close to the ground. Some embodiments of the invention will be described below in greater detail on the basis of the accompanying drawings.

DESCRIPTION OF EMBODIMENTS

Figure 1A:
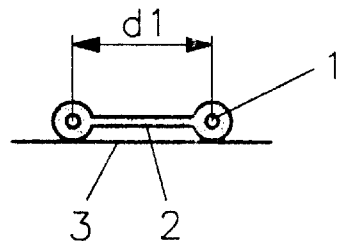
FIGS. 1a and 1b show schematically a particular embodiment of the sensor arrangements.
Figure 1B:
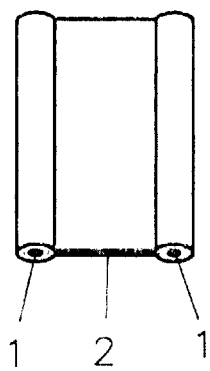

FIGS. 1a and 1b show the sensor with the two electrodes 1 in the form of a two-conductor flat cable. An insulation layer 2 extends around the conductors 1 (electrodes) and forms a distance structure between the conductors 1. A metal shield 3 shields the electric measuring field with respect to the space below. With the selection of the distance d1, the layer thickness of the material 4 (FIG. 3) that can be measured can be determined.

Figure 2A:
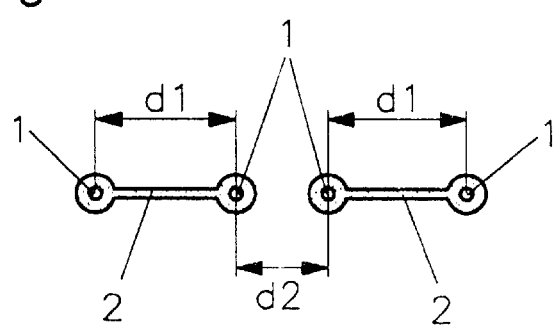
FIGS. 2a and 2b show another embodiment of the sensor arrangement.
Figure 2B:
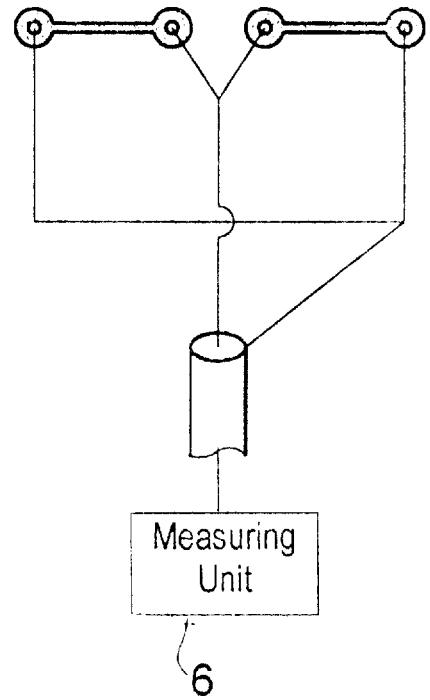

FIG. 2a and FIG. 2b show an advantageous embodiment of the probe in a three-conductor arrangement including two sensors arranged in parallel. With the distance d2 between the two two-conductor cables, which form the three-conductor arrangement, the impedance adaptation of the sensors to the measuring apparatus can be advantageously controlled. FIG. 2b shows the circuit arrangement for the four conductors of such a triple electrode arrangement and the connection thereof to a measuring apparatus 6.

Figure 3:
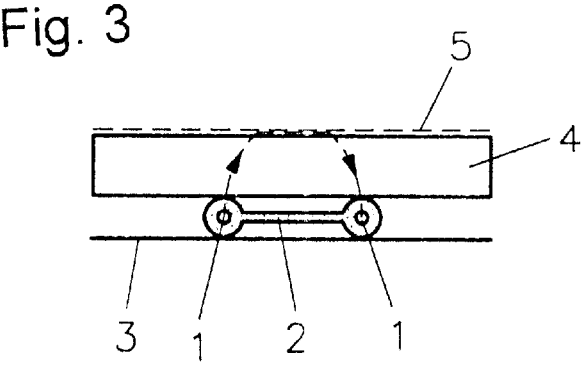
FIG. 3 shows the sensor arrangement below the layer, which is to be monitored and which is covered by a metal layer.

FIG. 3 shows the water permeable layer 4, which is to be measured, on top of the probe 1 with a metal shield 3 disposed below the probe and a metal shield 5 disposed on top of the layer 4 for delimiting the electrical field (measuring field).

By way of calibration measurements, the measured dielectricity coefficients are assigned to various water contents of the layer.

If the sensor is used in connection with layers for the detection of icing conditions, the dielectric coefficients in different ranges are assigned to the conditions dry, moist and iced.

An embodiment of the sensor with two conductors separated by a web is about 60 mm wide and 700 mm long and about 1.5 mm thick. With a d1 of 15 mm and a d2 of 20 mm water contents, based on weight, in the range of 10% to 150% are measured with an accuracy of about ±5% even in a highly densified betonite. The metal shielding layer is an adhesive tape provided with aluminum. The sensor is a three conductor-type sensor.

For use as an ice detector, a filter mat of polyester fibers with an area weight of 300 g/m$^2$ and a thickness of 20 mm is used.

For the electrical connection between the sensor and the measuring unit 6, a 20 m long shielded cable can be used. The measuring unit 6 determines the DK values.

What is claimed is:

1. A moisture sensor for sensing the moisture in layers, said moisture sensor including a conductor arrangement comprising two parallel electrical cables, a measuring apparatus for determining dielectric coefficients connected to said conductor arrangement, each cable including two spaced conductors connected in a three-conductor circuit, in which the conductors of said two cables disposed adjacent each other are at the same potential the space between the two inner conductors of said cables being selected so as to provide for a certain impedance of said conductor arrangement, said electrical conductors of each cable being surrounded by an insulating material layer of a predetermined thickness and carrying at one side, which is remote from the layer whose dielectric coefficient is to be measured, a metal shielding layer, the space between said inner conductors, the thickness of the insulating material and said metal shielding layer determining the measurement field of the moisture sensor in the layer in which the moisture is to be sensed.

2. A moisture sensor according to claim 1, wherein said conductors with said insulating layer and said metal shielding are flexible.

3. A moisture sensor according to claim 1, wherein said conductors have a measuring field and they are arranged at a distance from each other, which is so selected, that the measuring depth of the measuring field is comparable to the thickness of the layer whose moisture content is to be determined.

4. A moisture sensor according to claim 1, wherein said conductors with the insulating layer and the metal shielding have a wave resistance which during measurement is adapted to the characteristic resistance of the measuring apparatus.

5. A moisture sensor according to claim 1, wherein a water permeable metal layer is disposed on top of the layer whose dielectric coefficient is to be monitored.

6. A moisture sensor according to claim 1, wherein said layer to be monitored consists of a porous water-retaining material.

7. A moisture sensor according to claim 6, wherein said moisture sensor is disposed adjacent the ground for determining ice formation on the ground and on objects close to the ground.

8. A moisture sensor according to claim 1, wherein said moisture sensor is disposed adjacent a betonite layer for determining the water content thereof.

* * * * *